United States Patent [19]

Schulz et al.

[11] Patent Number: 5,296,330

[45] Date of Patent: Mar. 22, 1994

[54] POSITIVE PHOTORESISTS CONTAINING QUINONE DIAZIDE PHOTOSENSITIZER, ALKALI-SOLUBLE RESIN AND TETRA(HYDROXYPHENYL) ALKANE ADDITIVE

[75] Inventors: Reinhard Schulz, Staufen-Wettelbrunn; Norbert Münzel, Heiterscheim, both of Fed. Rep. of Germany; Martin Roth, Giffers, Switzerland; Wilhelm Knobloch, Schwörstadt, Fed. Rep. of Germany

[73] Assignees: Ciba-Geigy Corp., Ardsley, N.Y.; OCG Microelectronics Inc., West Patterson, N.J.

[21] Appl. No.: 932,128

[22] Filed: Aug. 15, 1992

[30] Foreign Application Priority Data

Aug. 30, 1991 [CH] Switzerland .......... 2550/91
Feb. 12, 1992 [CH] Switzerland .......... 413/92

[51] Int. Cl.$^5$ .......... G03F 7/023; G03C 1/61
[52] U.S. Cl. .......... 430/191; 430/165; 430/192; 430/193
[58] Field of Search .......... 430/165, 191, 192, 193

[56] References Cited

U.S. PATENT DOCUMENTS

| | | |
|---|---|---|
| 2,965,611 | 12/1960 | Schwarzer . |
| 3,046,112 | 7/1962 | Schmidt et al. . |
| 3,106,462 | 10/1963 | Cottle . |
| 3,148,983 | 9/1964 | Endermann et al. . |
| 3,201,239 | 8/1965 | Neugebauer et al. . |
| 3,365,019 | 1/1968 | Bays . |
| 3,661,582 | 5/1972 | Broyde . |
| 4,036,644 | 7/1977 | Kaplan et al. . |
| 4,115,128 | 9/1978 | Kita . |
| 4,277,600 | 7/1981 | Mark et al. .......... 528/204 |
| 4,552,876 | 11/1985 | Jones et al. .......... 514/234 |
| 4,626,492 | 12/1986 | Eilbeck .......... 430/191 |
| 5,077,173 | 12/1991 | Schulz et al. .......... 430/191 |

FOREIGN PATENT DOCUMENTS

| | | |
|---|---|---|
| 0085761 | 8/1986 | European Pat. Off. . |
| 368421 | 5/1990 | European Pat. Off. . |
| 0416544 | 3/1991 | European Pat. Off. . |
| 0435437 | 7/1991 | European Pat. Off. . |
| 0443820 | 8/1991 | European Pat. Off. . |
| 2-180878 | 7/1990 | Japan . |
| 2-219812 | 9/1990 | Japan . |

OTHER PUBLICATIONS

Chem. Ber. 52 (1979) pp. 2077–2079.
Patent Abstract of Japan vol. 9, 276 60-121445, Nov. 1985.
Derwent Abstract 90-309568141 of JD 2219-812-A (Sep. 1990) "Thermosetting, resin compositions for e.g. impregnating coil . . . ".

*Primary Examiner*—Charles L. Bowers, Jr.
*Assistant Examiner*—Christopher G. Young
*Attorney, Agent, or Firm*—William A. Teoli, Jr.

[57] ABSTRACT

Positive photoresist compositions comprising, in an organic solvent, at least
  a) one alkali-soluble resin,
  b) one photosensitive quinone diazide,
  c) one aromatic hydroxy compound of formula I

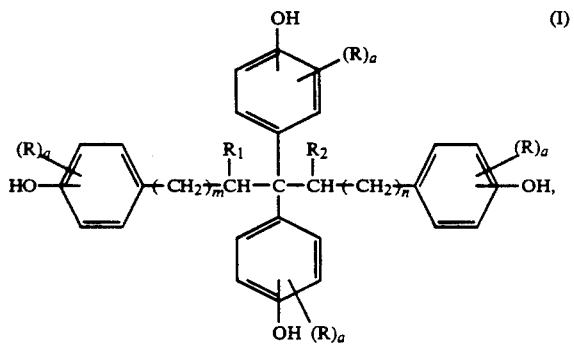

wherein each R is —H, $C_1$–$C_4$alkyl, $C_1$–$C_4$alkoxy, —$OCH_2C_6H_5$, —$OC_6H_5$ or —$COOC_1$–$C_4$alkyl, and $R_1$ and $R_2$ are each independently of the other H, $C_1$–$C_4$alkyl, —$C_6H_5$ or a cycloaliphatic 5- or 6-membered ring, a is an integer from 0 to 4, and m and n are each independently of the other 0, 1 or 2, which compound enhances the photosensitivity and/or the rate of development, and optionally
  d) additional customary modifiers,
are eminently suitable for making relief structures.

11 Claims, No Drawings

POSITIVE PHOTORESISTS CONTAINING QUINONE DIAZIDE PHOTOSENSITIZER, ALKALI-SOLUBLE RESIN AND TETRA(HYDROXYPHENYL) ALKANE ADDITIVE

The present invention relates to positive photoresist compositions which have enhanced resolution capability and reduced crystallisation tendency, using as compounds for enhancing photosensitivity (speed enhancers) specific tetra(hydroxyphenyl)alkanes, some of which are novel.

Photoresists is the name commonly given to photoimageable organic polymer materials which are used in photolithographic processes and related techniques, typically for making printing plates, printed electric circuits and circuit boards or, preferably, in microelectronics for making integrated semi-conductor components.

To produce circuit board structures in the fabrication of integrated microelectronic semi-conductor components, the semi-conductor substrate material is coated with the photoresist, and positive or negative photoresist structures are then obtained by imagewise exposure of the layer of photoresist and subsequent development. These photoresist structures act as mask for the techniques for producing the actual structures on the semi-conductor substrate, typically etching, doping, coating with metals or other semi-conductor or insulating materials. Afterwards the photoresist masks are usually removed. A host of such process cycles results in the formation of the circuit structures of the microchip on the substrate.

Conventional positive photoresists essentially comprise, in an organic solvent, at least one resin which is soluble in aqueous alkalies and a photosensitive quinonediazide which reduces the solubility of the resin in alkali, as well as other additional modifiers. When photoresist layers produced with such compositions are subjected to irradiation, the solubility of the resin in the alkali in the exposed areas is increased by photo-induced structural conversion of the quinone diazide into a carboxylic acid derivative, so that after development in aqueous alkaline developing baths, positive photoresist relief structures are obtained.

Among the essential performance properties of a photoresist, the properties in respect of radiation sensitivity, image resolution, contrast and storage stability are of particular importance.

A high sensitivity is important for ensuring brief radiation times in the process cycles, even if, for example, the apparatus employed only makes it possible to subject the resist to radiation of low intensity. The image resolution characterises up to what dimensions microfine image structures such as lines and spaces can be reproduced clearly separated by the photoresist. For example, the fabrication of VLSI circuits demands the reproduction of structural details in the order of magnitude of 1 μm and less. The contrast characterises the edge steepness and contour definition of the photoresist relief structures obtained after development.

The increasing miniaturisation in semi-conductor technology and microelectronics makes the most exacting demands of photoresist materials and of the relief structures to be reproduced, especially with respect to sensitivity, resolution and contrast, and also to bonding strength, mechanical and chemical stability, dimensional accuracy and resistance at elevated temperatures or other influences which can act upon the photoresist relief structures in the course of the further process steps.

To this end, the conventional positive photoresists normally comprise, in addition to the basic alkali-soluble resin and quinone diazide, a wide variety of modifiers for optimising the properties of the photoresist with respect to the requirements referred to above. Thus, for example, aromatic N-heterocyclic compounds are disclosed as sensitivity-enhancing additives in U.S. Pat. No. 3,661,582 and U.S. Pat. No. 3,365,019, including benzotriazole or halogenated benzotriazole derivatives. According to the teaching of U.S. Pat. No. 4,036,644 and U.S. Pat. No. 4,115,128, aliphatic compounds containing one or more carboxyl groups and organic cyclic anhydrides are used for the same purpose. Tetrahydroxyphenols are proposed as additives in EP-A-0 416 544. In U.S. Pat. No. 4,626,492, trihydroxybenzophenones are disclosed as particularly effective additives for enhancing sensitivity and the rate of development, especially 2,3,4-trihydroxybenzophenone. These compounds, however, are unable to satisfy the increasing demands in all respects. The effect of the increase in the rate of development by additives which carry hydrophilic or acid groups, as in the case of polyhydroxylated benzene derivatives, rests essentially on an increase in the solubility of the resist in aqueous-alkaline media. The simple addition of solubility-enhancing additives to the photoresist, and also the use of faster developers of higher ion concentration, has the drawback that, during development, increased attack of the unexposed areas of the resist occurs. The loss of resist coating from the unexposed areas is increased, i.e. the layer thickness of the remaining photoresist relief structures is diminished. Furthermore, the difference in solubility between exposed and unexposed areas becomes poorer, resulting in a diminution of contrast, i.e. a reduction in edge steepness and contour definition and hence in image quality.

Finally, in EP-A 0 435 437 it is proposed to use specific hydroxylated bis(diphenyl)methane compounds for enhancing photosensitivity.

It has now been found that the use of specific tetra(-hydroxyphenyl)alkanes in positive photoresist formulations markedly increases the photosensitivity and/or the rate of development without impairment of the customary properties, especially image quality.

Accordingly, the invention provides positive photoresist compositions comprising, in an organic solvent, at least a) one alkali-soluble resin,
b) one photosensitive quinone diazide,
c) one aromatic hydroxy compound of formula I

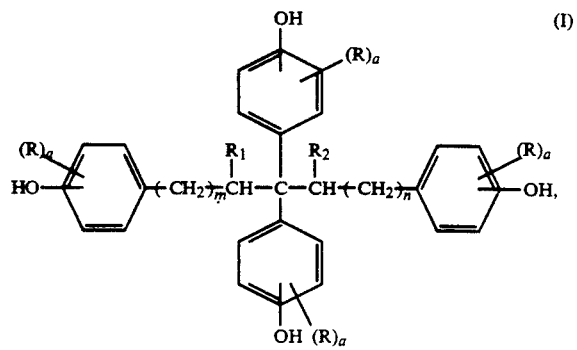

wherein each R is —H, $C_1$–$C_4$alkyl, $C_1$–$C_4$alkoxy, —OCH$_2$C$_6$H$_5$, —OC$_6$H$_5$ or —COOC$_1$–$C_4$alkyl, and $R_1$ and $R_2$ are each independently of the other H, $C_1$–$C_4$alkyl, —C$_6$H$_5$ or a cycloaliphatic 5- or 6-membered ring, a is an integer from 0 to 4, and m and n are each independently of the other 0, 1 or 2, which compound enhances the photosensitivity and/or the rate of development, and optionally d) additional customary modifiers.

$C_1$–$C_4$Alkyl and $C_1$–$C_4$alkoxy are typically methyl, ethyl, n-propyl, isopropyl, n-butyl or tert-butyl and, respectively, methoxy, ethoxy, n-propoxy, isopropoxy, n-butoxy or tert-butoxy.

Preferred compounds of formula I are those wherein R and $R_1$ are —H and a is 0 and m and n are 1 or 2.

Component c) is most preferably a compound of formula II

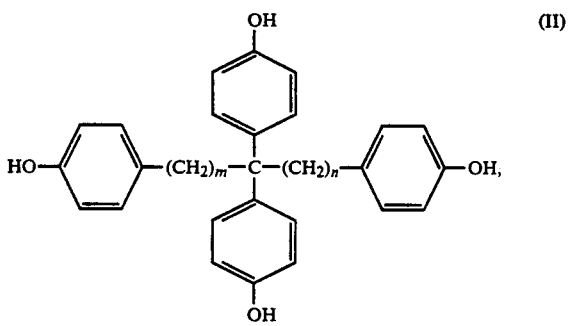

wherein m and n are each independently of the other 1, 2 or 3.

The invention also relates to the use of the compounds of formula I as additives for enhancing the photosensitivity and/or rate of development in positive photoresist compositions based on alkali-soluble resins and light-sensitive quinone diazides.

With respect to the main components, the novel positive photoresist compositions correspond substantially to the known and commercially available photoresists. They comprise, in an organic solvent, an alkali-soluble resin, a photosensitive quinone diazide and other customary optional additives with which the properties of the photoresist can be adjusted to the specific end-use requirements.

The photoresist composition conveniently contains component (c) in a concentration of 1 to 20%, based on the total solids content of said photoresist composition.

Compounds of formula II, wherein m and n are 2, are particularly preferred.

The novel positive photoresist compositions contain an alkali-soluble resin as resin component a), typically a novolak resin which is obtained by condensing phenol or a phenolic compound with an aldehyde.

Illustrative examples of phenolic compounds are phenol, cresols, xylenols, ethyl, propyl, butyl and phenyl phenols, resorcinol, pyrocatechol, hydroquinone, bisphenol A and pyrogallol.

Illustrative examples of aldehydes are formaldehyde, acetaldehyde, benzaldehyde and terephthalaldehyde.

Preferred resins are cresol-formaldehyde resins for the preparation of which o-, m- or p-cresol or mixtures of these isomers are used in any or given ratios. The preparation of such resins and their use in positive photoresists is described in U.S. Pat. No. 4,377,631.

The novel photoresist compositions will normally contain the resin component in an amount of about 50–95%, based on the total solids content of the photoresist composition.

The other alkali-soluble resins frequently used in positive photoresists can also be used. These resins include polyvinyl phenols and polyglutarimides, copolymers of styrene and α-methylstyrene with maleimide as well as copolymers of N-(p-hydroxyphenyl)maleimide and olefins. It is also possible to use silylated alkali-soluble polymers which have a greater resistance to plasma etching.

Other suitable alkali-soluble resins are derived typically from acrylic acid, methacrylic acid, styrene, maleic anhydride, maleimide, vinyl acetate, acrylonitrile and derivatives of these compounds, as well as mixtures thereof for preparing the corresponding copolymer.

To enhance their allround properties, such as storage stability, rate of development and/or heat resistance, further modifiers known to the skilled person can be added to the resins suitable for use in the practice of this invention.

The photosensitive quinone diazides contained in positive photoresists are quinone diazide sulfonic acid esters, typically esterification products of 2,1-naphthoquinone-1-diazide-4- or -5-sulfonic acid or, preferably, of 1,2-naphthoquinone-2-diazide-4- or -5-sulfonic acid, with low molecular aromatic or aliphatic hydroxy compounds. Such naphthoquinone diazide sulfonic acid esters are disclosed, inter alia, in U.S. Pat. Nos. 3,046,112, 3,106,462, 3,148,983 and 3,201,239, and also in EP 0 085 761. The light-sensitive components mainly used in positive photoresists are naphthoquinone diazide sulfonic acid esters of hydroxybenzophenones, in particular 2,3,4-trihydroxybenzophenone or 2,3,4,4'-tetrahydroxybenzophenone. Also useful are the corresponding esters of polyhydroxylated benzenes, including the isomers of trihydroxybenzene, typically 1,2,3-, 1,2,4- and, preferably, 1,3,5-trihydroxybenzene, and also polyhydroxylated biphenyls, for example 1,3',4,5',6-pentahydroxybiphenyl. Illustrative examples of such benzophenones and biphenyls are disclosed in EP-A 335 836.

Exemplary of hydroxy compounds are cresols, xylenols, resorcinol, pyrocatechol, 2,2'- and 4,4'-dihydroxybiphenyl, hydroquinone, pyrogallol, phloroglucinol, 4,4'-dihydroxybenzophenone, bis(4-hydroxyphenyl)ether, bis(4-hydroxyphenyl)sulfide, bis(2,4-dihydroxyphenyl)sulfide, bis(4-hydroxyphenyl)sulfone, 2,3,4-trihydroxybenzophenone, 2,4,4'-trihydroxybenzophenone, 2,3,4,4'-tetrahydroxybenzophenone, 2,2',4,4'-tetrahydroxybenzophenone, 2,2',3,4,4'-pentahydroxybenzophenone, 2,2',3,4,5'-pentahydroxybenzophenone, 2,3,3',4,5-pentahydroxybenzophenone, 2,3,3',4,4',5-hexahydroxybenzophenone, 2,3',4,4',5',6-hexahydroxybenzophenone, methyl, ethyl and propyl gallate, 2,2-bis(2,4-dihydroxyphenyl)propane, 2,2-bis(2,3,4-trihydroxyphenyl)propane, cresol-novolak resins, resorcinol-acetone resins, pyrogallol-acetone resins or polyvinyl-phenol resins. Combinations and mixtures of the naphthoquinone diazides listed above can also be used.

Of the light-sensitive naphthoquinone diazides, the 5-sulfonic acid esters are mainly used. These compounds have a broad absorption in the near to medium range UV wavelength with maxima at c. 400 nm and c. 340 nm. Strong emission lines of the mercury lamps normally used in the projection apparatus lie in this wavelength range, including the lines at c. 380 nm, 365 nm and 405 nm. The 4-sulfonic acid esters have absorption maxima at c. 380 nm and 300 nm, and are therefore more suitable for medium- to short-wave UV radiation, for example the mercury emission line at 313 nm.

The positive photoresists normally contain the quinone diazides in an amount of c. 5–50% by weight, based on the total solids content of the photoresist solution.

Other quinine diazides which can also be used are typically monomeric and dimeric 2-diazo-1,3-diketones, α-phosphoryldiazocarbonyl compounds and also benzoquinone diazide derivatives.

Particularly preferred esterification products are naphthoquinone sulfonic acid esters of 2,3,3-trihydroxybenzophenone, 2,3,4,4'-tetrahydroxybenzophenone, bis(4-hydroxyphenyl)sulfone, 4,4'-dihydroxybenzophenone or bis(2,4-dihydroxyphenyl)sulfide and, preferably, 2,3,4-trihydroxybenzophenone and 2,3,4,4'-tetrahydroxybenzophenone.

Esterification products of 1,2-naphthoquinone-2-diazide-5-sulfonic acid with a polyhydroxylated benzophenone or biphenyl are particularly preferred.

Esterification products of 1,2-naphthoquinone-2-diazide-4-sulfonic acid or 1,2-naphthoquinone-2-diazide-5-sulfonic acid or of 2,1-naphthoquinone-1-diazide-4- or -5-sulfonic acid with a polyhydroxylated compound of formula I above can also be used as photootosensitive quinone diazides in positive photoresist formulations. Such esterification products are novel and therefore also constitute an object of this invention.

Preferred esterification products are those of 1,2-naphthoquinone-2-diazide-5-sulfonic acid with a compound of formula I, wherein m and n are 1 or 2.

Such esterification products are eminently suitable photoactive components in positive photoresist formulations and have good allround performance properties, in particularly enhanced resolution capability and enhanced storage stability, and also a reduced crystallisation tendency in such formulations.

The novel esterification products can be prepared by per se known processes by reacting a 2,1-naphthoquinone-1-diazide-4- or -5-sulfonyl halide or a 2-naphthoquinone-2-diazide-4-or -5-sulfonyl halide, preferably a sulfonyl chloride, with a compound of formula I in about stoichiometric proportions or in excess, conveniently in an inert organic solvent and at elevated temperature; or alternatively by reacting a lower alkyl ester, typically a methyl or ethyl ester, of the appropriate naphthoquinone diazide-4- or -5-sulfonic acid, at elevated temperature, expediently while simultaneously removing the lower alkyl alcohol which forms during the reaction.

Suitable organic solvents are basically all inert solvents, typically aliphatic ketones, such as acetone, methyl ethyl ketone or methyl isobutyl ketone, also cyclohexanone, aliphatic esters, such as ethyl, propyl or butyl acetate, ethers, including dioxane, diethyl ether or tetrahydrofuran, and γ-butyrolactone, aliphatic or aromatic hydrocarbons, typically hexane, octane, chlorobenzene, dichlorobenzenes, toluene, xylenes or nitrobenzene, and formamide, dimethyl formamide, N-methylpyrrolidone or mixtures of such solvents.

A number of compounds of formula I, namely unsubstituted and 3-chloro 5-methyl- or 5-ethyl-substituted 1,2,2,3-tetrakis(2- or 4-hydroxyphenyl)propane derivatives [$R_1$, $R_2$=H; m and n=0; a=0 or 1] are known and disclosed in U.S. Pat. No. 2,965,611. The other compounds of formula I are, however, novel. They may be conveniently obtained by condensing a hydroxybenzaldehyde (e.g. para-hydroxybenzaldehyde) with an aliphatic ketone, typically with acetone, to give an unsaturated chalcone derivative, which is reacted by regioselective reduction of both C-C double bonds in the ketone radical and subsequent reaction of the resultant bis(hydroxyphenyl)ketone, e.g. 1,5-bis(p-hydroxyphenyl)pentan-3-one, with an excess of phenol by acid catalysis, to give the tetra(hydroxyphenyl)alkane of formula I, conveniently 1,3,3,5-tetra(p-hydroxyphenyl)-pentane.

Some of the requisite starting bis(hydroxyphenyl)ketones are also known and can be obtained by per se known processes. Examples are described in Chem. Ber. 52 (1919), p. 2078 or in U.S. Pat. No. 4,552,876, Example 17.

The compounds of formulae I and II are useful starting materials which may be used not only for the utility already stated (synthesis of naphthoquinone diazide esters and use as additives in photoresists), but also for the preparation of highly crosslinkable epoxy resins by glycidylising the (tetrahydroxyphenyl)alkanes of formula I and subsequent curing. Such tetrahydroxyphenols can also be used as hardeners for epoxy resins; and the products cured with them have a high glass transition temperature (Tg) and good mechanical properties as well as superior resistance to chemicals. Furthermore, these polyphenols can be used for synthesising tetracyanate esters as resins for the preparation of heat-resistant thermosetting plastics or as chain branchers for random branched polycarbonates according to DE-OS 3 035 204.

Suitable solvents for the preparation of the photoresist solution are basically all solvents in which the solid photoresist components such as alkali-soluble resin, the quinone diazides and additional optional modifiers are sufficiently soluble, and which do not undergo irreversible reaction with these components. Exemplary of such suitable solvents are aliphatic ketones, typically methyl ethyl ketone or cyclohexanone, aliphatic esters, typically butyl acetate, ethers such as tetrahydrofuran, alcohols such as n-propanol or isopropanol, mono- or diethers as well as mixed ether-ester derivatives of glycol compounds, such as of ethylene glycol, diethylene glycol or propylene glycol, and also monooxocarboxylates, conveniently ethyl lactate or ethyl 2-ethoxypropionate. Aliphatic and aromatic hydrocarbons such as n-hexane and xylene may also be used as solvents. Mixtures of the above mentioned solvents are also often used. Photoresist solvents often contain ethoxyethyl acetate, propylene glycol methyl ether acetate or ethylene glycol dimethyl ether. The amount of solvent is usually 40–95% of the total photoresist solution.

The further conventional modifiers which may also be added to the novel photoresist formulations include typically substances and dyes which afford protection against scattering radiation, flow control agents, plasticisers, adhesion promoters, further film-forming resins, speed enhancers, surfactants and stabilisers. The skilled person is sufficiently familiar with such modifiers, which are widely described in the relevant technical literature. The total amount of such modifiers does not exceed 25% by weight, based on the total solids content of the photoresist solution.

The novel photoresist formulations typically contain 50–90% by weight, preferably 60–80% by weight, of alkali-soluble resin, 5–30% by weight, preferably 10–25% by weight, of quinone diazide [component b)], 5-20% by weight, of component (c), and 0-30% by weight, preferably 0.1-5% by weight, of other modifiers, in each case based on the total solids content.

The novel positive photoresist compositions are formulated in per se known manner by mixing or dissolving the components in the solvent or mixture of solvents and adding component (c). It is equally possible to add the appropriate amount of component (c) to commercially available, ready-formulated positive photoresist formulations. After dissolving the components in the solvent, the photoresist solution—depending on the requirement made of the particle freedom—is filtered through a membrane filter having a pore size of 0.1-1 μm. Normally the total solids content of the photoresist will be adjusted to the desired layer thickness and coating method.

The application of the novel positive photoresist compositions is made by known techniques and using the conventional apparatus for the purpose. First, the photoresist is applied to the substrate and dried. Suitable substrates are semi-conductor wafers such as silicon wafers which may be coated with a layer of silicon dioxide, silicon nitride or aluminium. Other standard materials used for making miniaturised circuits, such as germanium, gallium arsenide, ceramics or metal-coated ceramics, are also suitable.

Coating is normally effected by dipping, spraying, roller coating or spin-coating. In this last mentioned and most often used coating method, the resultant layer thickness is dependent on the viscosity of the photoresist solution, the solids content and the rate of spin-coating. So-called spinning curves are plotted for the respective photoresist, from which curves it is possible to determine the resist layer thicknesses as a function of viscosity and spin speed. The layer thicknesses of positive photoresists are typically in the range of 0.5-4 μm, more particularly of 0.6-2.0 μm.

After coating the photoresist on to the substrate, it is normally dried in the temperature range from 70° to 130° C. Ovens or hot plates can be used for drying. The drying time in an oven is generally from about 15 to 45 minutes, and is from 0.5 to 4 minutes when using a hot plate. Resist layers with a thickness of 0.5-2 μm are preferably dried for about 1 minute at about 100° C. on a hot plate.

The dried photoresist is then exposed imagewise through a mask, applying radiation having a wavelength in the range from about 300 to 450 nm. Exposure can be made polychromatically or monochromatically. It is preferred to use commercial apparatus such as scanning projection exposure apparatus, contact and distance exposure apparatus or wafer steppers.

The irradiated substrates coated with the photoresist are finally developed with an aqueous-alkaline developer solution, typically by dipping or spraying, until the resist has been completely dissolved from the imagewise-exposed areas. It is possible to use different developer formulations which belong either to the class of the metal ion-containing or metal ion-free photoresist developers. Metal ion containing developers are typically aqueous solutions of sodium hydroxide or potassium hydroxide which may additionally contain pH regulators and buffers, such as phosphates or silicates, as well as surfactants and stabilisers. Metal ion-free developers are aqueous solutions of typically organic bases such as tetramethylammonium hydroxide or tetraethylammonium hydroxide or choline, and also primary, secondary or tertiary amines, such as ethylamine, propylamine, diethylamine, dipropylamine, trimethylamine and triethylamine, and amino alcohols, such as diethanolamine and triethanolamine. The development times depend on the exposure energy, the strength of the developer, the type of development, the predevelopment drying temperature and the development temperature. In immersion development the development times are typically about 1 minute. Development is normally stopped by dipping in, or spraying with, deionised water. Development is often followed by a post-exposure bake at about 120°-180° C.

The relief structures obtained with the novel photoresist compositions exhibit excellent image resolution to below 1 μm with high contrast, superior edge steepness and contour definition. There is minimum loss of layer thickness in the unexposed areas. Furthermore, the novel photoresist compositions have an enhanced resolution capability and a reduced tendency to crystallisation, as well as enhanced photosensitivity. In the following procedures for the production of integrated semi-conductor circuits, such as etching with acid or in plasma, doping or coating, they exhibit excellent properties and ensure effective protection of the areas of the substrate covered with the photoresist relief structures.

EXAMPLES

Preparation of naphthoquinone diazides

Example 1

12.3 g of 2,3,4,4'-tetrahydroxybenzophenone and 40.3 g of 1,2-naphthoquinone-2-diazide-5-sulfonyl chloride are dissolved in 300 ml of γ-butyrolactone. With stirring, 15.2 g of triethylamine, dissolved in 50 ml of acetone, are added dropwise to this solution. The temperature is kept at 25° C. during the reaction, and the dropwise addition is complete after 30 minutes. The reaction mixture is stirred for 3 hours and then added to 1500 ml of 1% HCl. The precipitate is isolated by filtration, washed with water and dried, giving 39.7 g of the esterification product, which consists of a mixture of the mono- and tetraesters as well as different isomers of the di-and triesters.

Example 2

10 g of 2,4,6,3',5'-biphenylpentol (pentahydroxybiphenyl) and 40.2 g of 1,2-naphthoquinone-2-diazide-5-sulfonyl chloride are dissolved in 500 ml of acetone. A solution of 15.2 g of triethylamine in 50 ml of acetone is added dropwise over 30 minutes. The reaction mixture is stirred for 3 hours at 25° C. The product is precipitated in 2.5 liters of 1% HCl, and the precipitate is isolated by filtration and dried, giving 38.7 g of an esterification product, which consists of a mixture of the mono- and tetraesters as well as different isomers of the di- and triesters.

Preparation of the novolaks

EXAMPLE 3 (resin 1)

0.13 g of oxalic dihydrate are added to 40 g of m-cresol, 60 g of p-cresol and 49.0 g of a 37% aqueous solution of formaldehyde in a 3-necked flask, and the mixture is then refluxed for 15 hours at 100° C. After cooling to room temperature, a vacuum is applied (5 torr;=6.665.10$^2$ Pa), and the temperature is slowly raised to 200° C., while distilling water and residual monomers from the reaction mixture. A novolak with an average molecular weight (Mw) of 7100 (=resin 1) is obtained.

EXAMPLE 4 (resin 2)

0.05 g of oxalic dihydrate are added to 60 g of m-cresol, 40 g of p-cresol and 48.6 g of a 37% aqueous solution of formaldehyde in a 3-necked flask, and the mixture is then refluxed for 15 hours at 100° C. After cooling to room temperature, a vacuum is applied (30 torr; =39.99.$10^2$ Pa), and the temperature is slowly raised to 150° C., while distilling water and residual monomers from the reaction mixture. A novolak with an average molecular weight (Mw) of 7350 is obtained. This novolak is fractionated as follows:

30 g of the novolak are dissolved in a mixture of 15 g of ethyl cellosolve acetate and 90 g of methanol, and 30 g of water are added and the mixture is stirred. The mixture is left to stand, whereupon phase separation occurs. The lower phase is separated and residual water and methanol are removed from it by vacuum distillation. A fractionated novolak with an average molecular weight of 10 250 is obtained (=resin 2).

Lithographic tests

Formulations 5 g of each of the quinone diazides of Examples 1 and 2, 20 g of a novolak and the compound of formula I indicated in Table 1 [THPP] are dissolved in 75 g of ethyl cellosolve acetate, and the resist solutions are filtered through a microfilter with a pore size of 0.2 μm.

TABLE 1

| Example | Novolak | Quinone diazide | THPP (component c) |
|---|---|---|---|
| 5 | resin 1 | Ex. 1 | 2 g |
| 6 | resin 1 | Ex. 2 | 2 g |
| 7 | resin 2 | Ex. 1 | 4 g |
| 8 | resin 2 | Ex. 2 | 5 g |

THPP=1,3,3,5-tetra(p-hydroxyphenyl)pentane [of formula II, wherein m and n are 2].

Lithographic results

The photoresist solutions of Table 1 are spin-coated at a speed of c. 5000 min$^{-1}$ on to silicon wafers, so that, after drying at 90° C./60 seconds on a vacuum hot plate, a layer thickness of 1.23 microns is obtained. The coated wafers are exposed through a resolution test mask with a model FPA-1550 Canon line stepper and then given a post-exposure bake for 120 seconds at 110° C. on the hot plate. Development is then carried out by the puddle method for 60 seconds with an aqueous 2.38% solution of tetramethylammonium hydroxide. After rinsing with water and spin drying, the wafers are investigated under a scanning electron microscope for light sensitivity, resolution and development residues between the resist lines. The minimum exposure energy (light sensitivity Eo in mJ/cm$^2$) and the resolution (in μm) are measured. The results are set forth in Table 2.

TABLE 2

| Example | Light sensitivity E (mJ/cm$^2$) | Resolution (μm) | Residues |
|---|---|---|---|
| 9 (of Ex. 5) | 120 | 0.55 | none |
| 10 (of Ex. 6) | 105 | 0.5 | none |
| 11 (of Ex. 7) | 205 | 0.52 | none |

TABLE 2-continued

| Example | Light sensitivity E (mJ/cm$^2$) | Resolution (μm) | Residues |
|---|---|---|---|
| 12 (of Ex. 8) | 170 | 0.52 | none |

Compared with known aromatic hydroxy compounds, e.g. 2,4,6,3',5'-pentahydroxybiphenyl or 2,3,4,3',4',5'-hexahydroxybenzophenone, the positive photoresist formulations obtained with THPP [1,3,3,5-tetra(p-hydroxyphenyl)pentane] used in the invention and the products obtained therefrom are distinguished by superior resolution without formation of residues. Compared with a resist prepared without the addition of a hydroxy compound, the light sensitivity is greatly enhanced.

EXAMPLE 13

Preparation of a novel quinone diazide from 1,2-naphthoquinone-2-diazide-5-sulfonic acid and 1,3,3,5-tetra(p-hydroxyphenyl)pentane 5.0 g of 1,3,3,5-tetra(p-hydroxyphenyl)pentane (THPP) and 9.16 g of 1,2-naphthoquinone-2-diazide-5-sulfonyl chloride are dissolved in 50 ml of γ-butyrolactone. With stirring, 3.52 g of triethylamine, dissolved in 40 ml of acetone, are added dropwise to this solution. The temperature is kept at 25° C. during the reaction. The reaction mixture is stirred for 5 hours and then added to 400 ml of 1% HCl. The precipitate is isolated by filtration, washed with water and dried, giving 11.5 g of an esterification product, which consists of a mixture of the mono- and tetraesters as well as different isomers of the di-and triesters.

EXAMPLES 14 AND 15

Formulations (lithographic tests

The tested formulations of 5 g each of a quinone diazide of Examples 1 and 2, 20 g of a novolak (of Examples 3 and 4) and, in Example 15, additionally 4 g of THPP (of formula II), are indicated in Table 3.

TABLE 3

| Example | Novolak | THPP | Diazide of |
|---|---|---|---|
| 14 | resin 1 | without | Example 13 |
| 15 | resin 2 | 4 g | Example 13 |

EXAMPLES 16 AND 17

Lithographic results

The lithographic test is carried out in accordance with the procedure of Examples 9–12. In addition, the crystallisation tendency of the respective naphthoquinone diazide of Example 13 is evaluated in an accelerated ageing test after 30 days at 40° C. The results are summarised in Table 4.

TABLE 4

| Example | Light sensitivity (mJ/cm$^2$) | Resolution (μm) | Residues | Crystallisation |
|---|---|---|---|---|
| 16 (of Ex. 14) | 155 | 0.55 | none | none |
| 17 (of EX. 15) | 195 | 0.52 | none | none |

The positive photoresist compositions obtained are distinguished by very high resolution without crystallisation tendency after storage for 30 days at 40° C. In contrast to the corresponding positive photoresist compositions which contain the above resin 1 and the esterification product of Example 1 or 2, but without the use of THPP, the novel compositions exhibit no crystallisation tendency.

EXAMPLE 18 (Preparation of THPP)

5 kg (18.7 mol) of 1,5-bis(p-hydroxyphenylpenta-1,4-dien-3-one, which has been obtained by condensation of 2 mol of p-hydroxybenzaldehyde with 1 mol of acetone with acid catalysis, are dissolved in 32 liters of DMF (dimethyl formamide) and the solution is hydrogenated with hydrogen at room temperature using 250 g of Raney nickel (moist with ethanol) as catalyst, at a pressure of 5 bar (=$5.10^5$ Pa). The hydrogen uptake is 841.16 liters (hydrogenation time 2.5 hours). The solvent is removed by distillation, leaving 5 kg of a brown viscous oil [1,5-bis(p-hydroxyphenyl)pentan-3-one], which is used direct for the next step. 1015.5 g (3.76 mol) of the intermediate so obtained [1,5-bis(p-hydroxyphenyl)pentan-3-one], 1767.7 g (24.1 mol) of phenol and 26.3 ml of 3-mercaptopropionic acid are charged to a 6 liter reaction flask equipped with stirrer, reflux condenser, thermometer and gas inlet for HCl gas as well as gas exit and attached HCl absorption unit, and the mixture is heated to 60° C. on a thermostatically controlled oil bath. HCl gas is introduced in a gentle stream over 1 hour, while keeping the temperature at 70° C. The reaction mixture is then stirred for 3 hours at this temperature without the introduction of HCl. This sequence of introducing gas for 1 hour and stirring for 3 hours is repeated three times. Then a further 500 g of phenol are added and the above sequence is repeated ten times. The total reaction time is 56 hours. The dark violet viscous reaction mass is diluted with 2000 ml of fused phenol and the solid product is isolated by filtration. The solid filter residue is suspended in 3000 ml of hot water, the suspension is filtered and the filter cake is washed well with hot water. The residue is dried under vacuum at 120° C. for 24 hours, giving 1451.4 g (=87.6% yield, based on ketone) of white-violet crystals of 1,3,3,5-tetra(p-hydroxyphenyl)pentane.

Melting point: 252° C. (determined by DSC); the product is readily soluble in acetone.

Phenolic HO groups: 9.469 mol/kg (theory 9.080 mol/kg);

Elemental analysis: calcd C 79.07% H 6.41%; found C 77.96% H 6.45%.

EXAMPLE 19

[1,5-bis(parahydroxyphenyl)-3,3-bis(4-hydroxy-3-methylphenyl)pentane]: 27.00 g (0.10 mol) of the intermediate 1,5-bis(parahydroxyphenyl)pentan-3-one of Example 18 (first part) above, 108.14 g (1.00 mol) of ortho-cresol and 1.50 ml of 3-mercaptopropionic acid are charged to a 750 ml reaction flask as described in Example 18 and the mixture is heated to 60° C. In accordance with the procedure described in Example 18, HCl gas is introduced from a bomb over 48 hours at periodic intervals. The reaction can be monitored by thin-layer chromatography on silica gel plates (eluant=methylene chloride:methanol 95:5). Upon termination of the reaction, no further educt is detectable.

The reaction product is taken up in ethyl acetate and the solution is extracted with an saturated aqueous solution of sodium bicarbonate until the reaction is neutral. The organic phase is dried over magnesium sulfate, filtered, and the solvent is stripped off on a rotary evaporator. Excess ortho-cresol is removed by high vacuum distillation, giving 60.68 g of a dark crude product which is first stirred in toluene, then the solid is taken up in methylene chloride, the product is filtered and vacuum dried at 50° C., giving 29.85 g (63.7% of theory) of orange crystals of 1,5-bis(parahydroxyphenyl)-3,3-bis(4-hydroxy-3-methylphenyl)pentane. For characterisation, a sample is recrystallised three times from methanol/water to give colourless crystals.

M.p.: 215.7° C. (determined by DSC).

Elemental analysis: calcd C 79.46% H 6.88%; found C 78.04% H 6.91%.

EXAMPLE 20

Use of the THPP of Example 18 as hardener

A flame-resistant epoxy resin (reaction product of a diglycidyl ether of bisphenol A with the corresponding brominated bisphenol A) (epoxy value: 2 eq/kg; FR 4 resin) is cured with THPP as hardener and 2-methylimidazole as accelerator by a standard method and laminates are prepared therefrom.

Amount of resin used: 25%, based on 100% solid resin.

Equivalent ratios: epoxy resin to THPP to 2-methylimidazole: 1.0 mol to 0.25 mol to 0.0032% by weight.

The glass transition temperature Tg of the laminates is 133° C., and the absorption of N-methylpyrrolidone (in %) is 0.50. The laminates have a low water and NMP absorption.

EXAMPLE 21

1,3,3,5-Tetra(p-glycidyloxyphenyl)pentane 313.0 g (0.71 mol) of the tetraphenol THPP (of Example 18), 1577.9 g (17.05 mol) of epichlorohydrin and 770 ml of 1-methoxy-2-propanol are charged to a 4.5 l reaction flask equipped with stirrer, thermometer, dropping funnel and heating bath, and the mixture is heated to 50° C. With good stirring, 233 g (2.91 mol) of a 50% aqueous solution of sodium hydroxide are added dropwise over 2.5 hours such that the temperature does not rise above 60° C. (cooling from time to time with ice-water is necessary). The suspension is stirred for 2 hours at 50°-60° C., a small amount of dry ice is added (to neutralise any excess base), and excess epichlorohydrin and solvent are removed by distillation under reduced pressure (80–130 mbar). To the still warm distillation residue are added 500 ml of isobutyl methyl ketone, then the suspension is stirred for 0.5 hour at room temperature and filtered. The filtrate is evaporated to dryness on a rotary evaporator and the residual brown residue (529.7 g) is freed from volatile matter in a flash distillation unit at 150° C. jacket temperature and under a vacuum of 0.01 mbar. Yield: 361.7 g (76% of theory, based on tetraphenol THPP) of 1,3,3,5-tetra(p-glycidyloxyphenyl)pentane as a solid brown resin.

Characterisation:

epoxy value: 5.5 mol/kg (91% of theory);

viscosity: 640 mPa.s at 120° C.;

GPC (polystyrene calibration: Mw=809; Mn=733; Mw/Mn=1.10

EXAMPLE 22

Blending 21% by weight of the product of Example 22 with a reaction product of a diglycidyl ether of bisphenol A with the corresponding tetrabromobisphenol A (FR 4 resin; epoxy value 2 eq/kg) and adding a hardener/accelerator mixture (dicyandiamide/2-

What is claimed is:

1. A positive photoresist composition comprising, in an organic solvent, at least
   a) one alkali-soluble resin,
   b) one photosensitive quinone diazide,
   c) one aromatic hydroxy compound of formula I

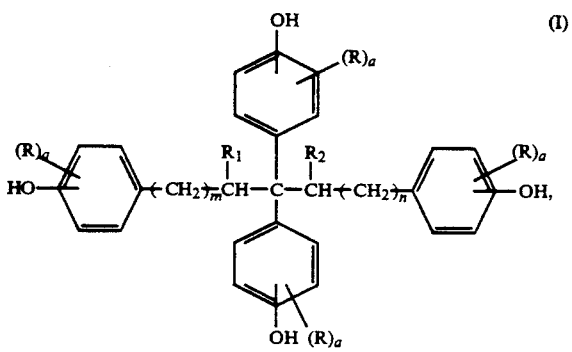

wherein each R is —H, $C_1$-$C_4$alkyl, $C_1$-$C_4$alkoxy, —$OCH_2C_6H_5$, —$OC_6H_5$ or —$COOC_1$-$C_4$alkyl, and $R_1$ and $R_2$ are each independently of the other H, $C_1$-$C_4$alkyl, —$C_6H_5$ or a cycloaliphatic 5- or 6-membered ring, a is an integer from 0 to 4, and m and n are each independently of the other 0, 1 or 2, which compound of formula (I) is present in the photoresist composition in an amount effective to enhance the photosensitivity and/or the rate of development of said composition.

2. A positive photoresist composition according to claim 1, wherein in formula I $R_1$ and $R_2$ are -H and m and n are 1 or 2.

3. A positive photoresist composition according to claim 1, wherein component c) is a compound of formula II

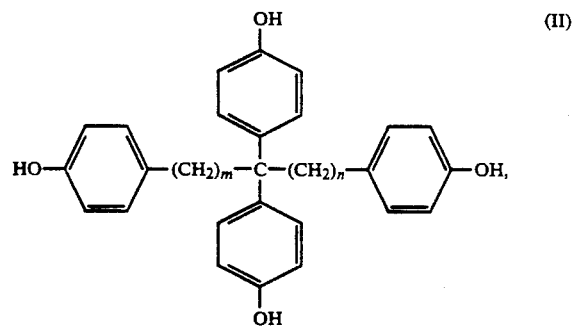

wherein m and n are each independently of the other 1, 2 or 3.

4. A positive photoresist composition according to claim 3, wherein m and n are 2.

5. A positive photoresist composition according to claim 1, which contains the compound of formula I in an amount of 0.5–30% by weight, based on the total solids content of said photoresist composition.

6. A positive photoresist composition according to claim 1, wherein component a) is a novolak resin.

7. A positive photoresist composition according to claim 6, wherein the novolak resin is a cresol-formaldehyde resin.

8. A positive photoresist composition according to claim 1, wherein component b) is an esterification product of 1,2-naphthoquinone-2-diazide-4-or -5-sulfonic acid with low molecular aromatic or aliphatic hydroxy compounds.

9. A positive photoresist composition according to claim 8, wherein the esterification product is an ester of 1,2-naphthoquinone-2-diazide-4- or -5-sulfonic acid with a polyhydroxylated benzophenone or biphenyl.

10. A photoresist composition according to claim 1 comprising
    50–90% by weight of component a),
    5–30% by weight of component b),
    5–20% by weight of component (c), and optionally
    0–30% by weight of modifiers, in each case based on the total solids content.

11. A positive photoresist composition according to claim 1, which further comprises d) additional customary modifiers.

* * * * *